United States Patent [19]

Maldonado et al.

[11] 3,996,106

[45] Dec. 7, 1976

[54] CHEMICAL PROCESS

[75] Inventors: Paul Maldonado, St. Symphorien D'Ozon; Max Charpentier, Montesson; Georges Glikmans, Meudon la Foret, all of France

[73] Assignee: Institut Francais du Petrole, des Carburants et Lubrifiants et Entreprise de Recherches et d'Activities Petrolieres Elf, France

[22] Filed: Nov. 6, 1974

[21] Appl. No.: 521,521

[30] Foreign Application Priority Data

Nov. 6, 1973  France .............................. 73.39396

[52] U.S. Cl. .................................. 195/30; 195/37; 195/40
[51] Int. Cl.² ........................................... C12D 1/04
[58] Field of Search ......................... 195/30, 37, 40

[56] References Cited

UNITED STATES PATENTS

| 3,717,549 | 2/1973 | Roberts | 195/37 |
|---|---|---|---|
| 3,873,424 | 3/1975 | Kimura et al. | 195/37 |

*Primary Examiner*—Alvin E. Tanenholtz
*Attorney, Agent, or Firm*—Bucknam and Archer

[57] ABSTRACT

This invention relates to the production of citric and/or isocitric acids. The production of citric and/or isocitric acids is effected by cultivating a citric and/or isocitric acid-producing yeast in a culture medium containing a compound selected from cyanoacetic acid, and organic and inorganic derivatives thereof. Increased yields of citric and isocitric acids are obtained using a process in accordance with the invention, preferably using a yeast of the genus Candida.

9 Claims, No Drawings

CHEMICAL PROCESS

This invention relates to processes for the production of citric and/or isocitric acids.

According to the present invention there is provided a process for the production of citric acid and/or isocitric acids, which comprises cultivating a citric and/or isocitric acid-producing strain of a yeast in a culture medium therefor, the medium comprising at least one source of carbon, at least one source of nitrogen, at least one inorganic compound, and cyano-acetic acid or an organic or inorganic derivative thereof in an amount sufficient to increase the production of citric and/or isocitric acids by the yeast.

Using a process in accordance with the present invention, large amounts of citric and/or isocitric acids can be produced in a relatively simple manner on an industrial scale, and at low cost, to give a high yield of products.

Cyanoacetic acid and its derivatives have a remarkable effect upon the citric and/or isocitric acid excretion of yeasts. Indeed, cyano-acetic acid and derivatives thereof, when present in a culture medium containing yeast cells, are assimilated by the yeast cells and give rise to analogues of Krebs cycle intermediates. These analogues modify the normal operation of the Krebs cycle, and this modification in general improves the excretion rates and yields of citric and isocitric acids by the yeast cells.

The amount of cyano-acetic acid or a derivative thereof, added to the culture medium is preferably between an effective amount and about 0.1% by weight.

Precise values for the concentration of cyano-acetic acid, or a derivative thereof, to be used are difficult to give, as they usually vary with the strain of yeast used and the culture conditions. Moreover, the concentration to be used may vary as a function of the time during the cultivation when the addition is made.

Although the cyano-acetic acid, or a derivative thereof, can be added to the nutrient medium, all at once or intermittently, it is usually preferred to add the particular compound at between 24 and 48 hours after the commencement of culture, corresponding to the end of the exponential growth phase of the yeast.

The following are examples of derivatives of cyano-acetic acid which can be used in accordance with the invention:

salts such as sodium and potassium cyanoacetates;
organic esters such as methyl and ethyl cyanoacetates; and
organic derivatives such as cyanoacetamide.

Yeasts which assimilate hydrocarbons and can be used in accordance with the present invention are preferably chosen from the genus Candida.

The culture medium can be synthetic or a naturel nutrient medium. The medium will generally include at least one source of carbon, at least one source of nitrogen and at least one inorganic compound. Suitable aqueous culture media usually contain a hydrocarbon or a mixture of hydrocarbons as the principal carbon source. These hydrocarbons are preferably straight-chain alkanes containing from 12 to 20 carbon atoms (n-paraffins).

Suitable nitrogen sources include various organic or inorganic compounds, such as urea, ammonium salts, for example ammonium chloride, ammonium sulfate, ammonium nitrate, ammonium phosphate, or ammonium acetate, one or more amino acids, and natural substances containing nitrogen, for example maize maceration liquor, yeast extract, meat extract, fish meal, or peptone, etc.

Inorganic compounds that can be present in the culture medium include magnesium sulfate, potassium dihydrogen phosphate, phosphoric acid, potash, iron sulfate, manganese sulfate, manganese chloride, calcium carbonate, calcium chloride, sodium carbonate, and potassium carbonate.

Moreover, it may be necessary to add one or more nutrients to the culture medium depending upon the yeast used. Examples of such nutrients are amino acids such as aspartic acid, threonine, methionine, iso-leucine, valine glutamic acid, and lysine, etc., and vitamins such as thiamin, nicotinic acid, and biotin, etc.

In certain cases, the addition of an emulsifying agent can increase the yield of citric and/or isocitric acids.

Culture of the yeast will generally be effected under aerobic conditions by stirring and aerating the culture medium, preferably at a temperature of from 20° to 40° C, and advantageously at from 25° to 35° C, conveniently at a pH of from 2 to 7, and preferably from 3 to 6.

The pH of the culture medium can be adjusted by the addition of a non-nitrated basic aqueous solution, for example of soda, potash, basic sodium carbonate or basic potassium carbonate.

Processes in accordance with the present invention use citric and/or isocitric acid-producing yeasts, mutant strains of yeasts of the genus Candida being preferred. Mutants can be obtained by physical techniques such as the use of X-rays or ultra-violet rays, or by chemical techniques such as the use of nitrosomethylurethane or nitrosoguanidine, which are well known for their mutagenous action.

When citric and/or isocitric acids have accumulated in the culture medium, they can be isolated therefrom by classical methods, for example as the insoluble calcium salts. This can be effected as follows:

After elimination of the yeast cells, a stoichiometric amount of calcium chloride, for example, is dissolved in the culture medium, corresponding to the amounts of citric and isocitric acids present. The medium can then be neutralised with aqueous ammonia, and the calcium citrate precipitated by heating.

The following Examples are given by way of illustration only.

EXAMPLE 1

(Comparison Example)

Preparation of the inoculum:

Seeding was carried out in a 100 ml flask, from an agar tube containing cells of *Candida lipolytica* TFP 29, of 20 ml of a liquid preculture medium having the following composition:

| | |
|---|---|
| $KH_2PO_4$ | 3.4 g/liter |
| $Na_2HPO_4 . 12H_2O$ | 1.7 g/l |
| $MgSO_4 . 7H_2O$ | 0.7 g/l |
| $(NH_4)_2SO_4$ | 4 g/l |
| $CaCl_2$ | 0.1 g/l |
| $FeSO_4 . 7H_2O$ | 2 mg/l |
| $CuSO_4 . 5H_2O$ | 5 µg/l |
| $H_3BO_3$ | 10 µg/l |
| $MnSO_4 . 7H_2O$ | 10 µg/l |
| $ZnSO_4 . 7H_2O$ | 10 µg/l |
| $(NH_4)_6Mo_7O_{24} . 4H_2O$ | 100 µg/l |
| $Co(NO_3)_2 . 6H_2O$ | 10 µg/l |

-continued

| | |
|---|---|
| Yeast extract | 100 mg/l |
| Tap water | to make up 1 liter |
| n-paraffin cut | $C_{12}-C_{20}$ 15 g/l |

After incubation for 36 hours at 30° C on a shaking table adjusted to a speed of 130 r.p.m., 10 ml of the resulting inoculum were used to seed 200 ml of a nutrient medium containing in a Fernbach 1.5 liter flask, the medium having the following composition:

| | |
|---|---|
| $KH_2PO_2$ | 2 g/l |
| $MgSO_4 . 7H_2O$ | 1 g/l |
| $NH_4NO_3$ | 2.5 g/l |
| $CaCO_3$ | 20 g/l |
| $FeSO_4 . 7H_2O$ | 0.2 g/l |
| $MnSO_4 . 7H_2O$ | 26 mg/l |
| Yeast extract | 100 mg/l |
| Tap water | to make up 1 liter |
| n-paraffin cut | 25 g/l |

After incubation for 36 hours under the previously described conditions, this medium was used as inoculum to seed a 2.5 l fermenter containing 1.2 l of a culture medium having the following composition:

| | |
|---|---|
| $KH_2PO_4$ | 4 g/l |
| $MgSO_4 . 7H_2O$ | 2 g/l |
| $NH_4NO_3$ | 5 g/l |
| $FeSO_4 . 7H_2O$ | 0.4 g/l |
| $MnSO_4 . 7H_2O$ | 52 mg/l |
| Thiamine hydrochloride | 1 mg/l |
| Tap water | to make up 1 liter |
| n-paraffin cut $C_{12}-C_{20}$ | 100 g/l |

The pH of the medium was adjusted to 4.5 by adding a molar aqueous solution of potassium carbonate while the medium was energetically agitated at 2,300 r.p.m. at 30° C and aerated under sterile conditions with a flow rate of 1 liter of air per minute per liter of medium.

At the end of 135 hours of cultivation, the concentration of citric and isocitric acids in the culture medium were:

| | |
|---|---|
| Citric acid | 60 g/l |
| Isocitric acid | 28 g/l |

EXAMPLE 2

The fermentation described in Example 1 was repeated with the addition of 100 mg/l of cyanoacetamide to the culture medium, at between thirty and forty hours after the commencement of cultivation. The concentrations of citric and isocitric acids excreted by the yeasts at the end of 135 hours were:

| | |
|---|---|
| Citric acid | 86 g/l |
| Isocitric acid | 32 g/l |

EXAMPLE 3

The fermentation described in Example 2 was repeated with the cyano-acetamide being replaced by 100 mg/l of cyano-acetic acid, the addition of the cyano-acetamide being between the thirtieth and fortieth hours of cultivation. The culture medium contained 200 g/l of an n-paraffin cut. The concentrations of citric and isocitric acids in the medium at the end of 225 hours were:

| | |
|---|---|
| Citric acid | 162 g/l |
| Isocitric acid | 68 g/l |

EXAMPLES 4 to 7

These Examples illustrate the cultivation of two different strains of yeast, namely *Endomycopsis lipolytica* D 1805 (ATCC 20,390) and *Candida lipolytica* (ATCC 8661) under the conditions described in Example 1, with the exception that the culture medium contained 165 g/l instead of 100 g/l of the n-paraffin cut and the duration of cultivation was 160 hours instead of 135 hours.

So that these Examples included comparisons, 100 mg/l of cyano-acetic acid were added to only one of each of the two culture media for each of the strains of yeast.

The result given hereinafter in the Table show the effect of cyano-acetic acid upon the excretion of citric and isocitric acids by different yeasts.

| Ex. | Yeast Strain | Culture medium | Citric acid g/l | Isocitric acid g/l | Total (Citric + isocitric acids) g/l |
|---|---|---|---|---|---|
| 4 | ATCC 20,390 | Control | 106 | 54 | 160 |
| 5 | ATCC 20,390 | + 100 mg/l cyanoacetic acid | 155 | 75 | 230 |
| 6 | ATCC 8,661 | control | 88 | 47 | 135 |
| 7 | ATCC 8,661 | + 100 mg/l cyanoacetic acid | 120 | 64 | 184 |

EXAMPLE 8

The fermentation described in Example 1 was repeated, and comparable results were obtained, using sodium cyano-acetate, potassium cyano-acetate, or an ester of cyano-acetic acid with an alcohol, at the same concentration as the cyanoacetamides in Example 2.

EXAMPLE 9

The fermentation described in Example 2 was repeated, and comparable results obtained, using one of the following yeasts of the genus Candida instead of *Candida lipolytica* W 29.

| *Candida* strain | No. |
|---|---|
| Lipolytica | IFP 102 |
| Lipolytica | IFP 88 |
| Lipolytica | ELF 8 |
| Lipolytica | ELF 19 |
| Lipolytica | ELF 25 |
| Lipolytica | ELF Mg-5 |
| Tropicalis | IFP 114 |

We claim:
1. A process for the production of at least one of citric and isocitric acids, which comprises cultivating a citric and isocitric acid-producing strain of a yeast in a culture medium therefor, the medium containing a compound selected from the group consisting of cyanoacetic acid, inorganic salts and organic esters thereof and the amide thereof, in an amount sufficient to increase the production of said citric acid isocitric acids by the yeast, accumulating at least one of said citric and isocitric acid in the culture medium and recovering said citric and isocitric acid therefrom.

2. A process according to claim 1, wherein the concentration of said compound in the culture medium is up to 0.1% by weight.

3. A process according to claim 1, wherein the yeast is of the species *Candida lipolytica* and the cultivation is effected in the presence of a hydrocarbon.

4. A process according to claim 3, wherein said compound is added to the culture medium after completion of the exponential growth phase of the yeast.

5. A process according to claim 3, wherein the hydrocarbon is a straight chain alkane containing from 12 to 20 carbon atoms.

6. A process according to claim 3, wherein the culture medium contains at least one nutrient for the yeast.

7. A process according to claim 6, wherein the nutrient is aspartic acid, methionine, glutamic acid or lysine.

8. A process according to claim 3, wherein cultivation is effected at a temperature of from 20° to 40° C at a pH of from 2 to 7.

9. A process according to claim 1, wherein yeast cells are separated from the culture medium, and the desired acid is recovered from the resulting medium.

* * * * *